United States Patent [19]
Leu

[11] Patent Number: 5,930,791
[45] Date of Patent: Jul. 27, 1999

[54] COMPUTERIZED BLOOD ANALYZER SYSTEM FOR STORING AND RETRIEVING BLOOD SAMPLE TEST RESULTS FROM SYMMETRICAL TYPE DATABASES

[76] Inventor: Sean Leu, 1203 Yorkshire Dr., Cupertino, Calif. 95014

[21] Appl. No.: 08/762,708

[22] Filed: Dec. 9, 1996

[51] Int. Cl.⁶ ................................................. G06F 17/00
[52] U.S. Cl. ...................... 707/8; 707/1; 707/3
[58] Field of Search .................. 395/608, 602; 707/1, 3, 8, 203; 422/81; 436/45; 705/3

[56] References Cited

U.S. PATENT DOCUMENTS

| | | | |
|---|---|---|---|
| 5,287,496 | 2/1994 | Chen et al. | 707/203 |
| 5,361,202 | 11/1994 | Doue | 705/3 |
| 5,392,209 | 2/1995 | Eason et al. | 707/3 |
| 5,495,606 | 2/1996 | Borden et al. | 707/3 |
| 5,526,517 | 6/1996 | Jones et al. | 707/8 |
| 5,528,492 | 6/1996 | Fukushima | 707/1 |
| 5,535,385 | 7/1996 | Griffin et al. | 707/3 |
| 5,546,580 | 8/1996 | Selinger et al. | 707/8 |
| 5,551,022 | 8/1996 | Tariq et al. | 707/8 |
| 5,577,239 | 11/1996 | Moore et al. | 707/3 |
| 5,620,898 | 4/1997 | Yaremko et al. | 436/45 |
| 5,665,312 | 9/1997 | Sperber et al. | 422/81 |
| 5,666,524 | 9/1997 | Kunkel et al. | 707/3 |
| 5,689,697 | 11/1997 | Edwards et al. | 707/3 |
| 5,694,591 | 12/1997 | Du et al. | 395/602 |
| 5,721,905 | 2/1998 | Elixmann et al. | 395/608 |

OTHER PUBLICATIONS

Graves et al., "Graph Database Systems", IEEE Engineering in Medicine and Biology Magagine, pp. 737–745, Nov. 1995.

Smith, "Brief Guide to Information Resources Supporting the Human Genome Project", IEEE Engineering in Medicine and Biology Magagine, pp. 760–761, Nov. 1995.

*Primary Examiner*—Wayne Amsbury
*Assistant Examiner*—Thuy Pardo

[57] ABSTRACT

Disclosed herein is a computerized blood analyzer system. The system includes a clinical analyzer CU and a blood analyzer AU. The clinical analyzer has a computer which issues commands and instructions to the AU as desired. These commands and instruction's include retrieval and storage commands and instructions. The blood analyzer unit AU is electronically connected to the CU and operates upon the commands and instructions of the CU. The AU generates test results which are stored in the computer. The computer has storage media for storing the results. The storage media comprises an aggregate database which includes at least two parts, namely a working database and an archived database. It is preferable in many case for the aggregate database to include a back-up database. Each of the databases stores the data in similar data fields, organization and structure comprising symmetrical-like databases. This enables a single set of commands and instructions to store and retrieve the data.

18 Claims, 5 Drawing Sheets

COMPUTERIZED BLOOD ANALYZER SYSTEM FOR STORING AND RETRIEVING BLOOD SAMPLE TEST RESULTS FROM SYMMETRICAL TYPE DATABASES

BACKGROUND OF THE INVENTION

1. Field of the Invention

This invention relates to methods and apparatus for analyzing biological fluid samples and storing related data. More particularly, this invention relates to the use of symmetrical-type data bases for storing and retrieving blood sample test results.

2. Previous Art

The recognition of the fact has caused blood analysis to become increasingly sophisticated. Typically, the blood analyzer system is computerized increasing the number of operations that can be performed, the number of patients that can be served as well as increasing the level of sophistication of the test themselves.

Typically, the computerized system includes an clinical analyzer unit (AU), and a computer unit (CU). The computer unit (CU) tells the analyzer unit (AU) what test are to be performed and on what samples. The AU performs the test accordingly and feeds back the data to the CU. Typically, the CU stores the data for later retrieval. There are many clinical analyzer units on the market which are capable of analyzing blood in the manner discussed above.

Blood, is a general term which includes blood serum and other separable components. AU's are often used to analyze the various blood components including blood serum. The composition of the various components is analyzed and used to evaluate a patient's health. In particular, it is often desirable to test for various elements, minerals and other matter to facilitate diagnosis and treatment of a patient's condition.

Over a period of a year, thousands, hundreds of thousands, and even millions of tests are performed on blood samples by a single CU. The results of these tests are stored by the CU after the testing is completed. These test results need to be sorted and searched using various search criteria. Sorted results, among other things, assist medical researchers and physicians in identifying particularized medical trends for a patient, for a group of patients, for a particular day, or for a geographical area and the like.

Data is a generic term used to described items, such as test results such as those treated by the AU, which are stored in a database. The test results as noted above are stored in the CU. Typically, the test results are stored in a single database.

One problem with a single database is that, over time, stored data may be too unwieldy to effectively search, sort and backup. To minimize problems associated with unwieldy databases, the use of multiple data bases have been proposed. Multiple data bases may be used to backup data and to assist in organization of the data. Each of these data bases are searched separately, yielding separate data for each database.

As the number of records has increased, there has developed a need to off load data from the everyday computer unit's memory, sometimes known as a working database. When the working database is full of data, such as the results, the functioning of the CU is slowed down considerably. The slowness of the CU can cause delay for doctors, or other health professionals, in getting results and delay in assisting the patients.

For these reasons, among others, some of the test results stored on the CU are achieved on other data bases. Typically, these archived data bases may not even be stored on the CU. The archived database may likely be on an entirely separate computer. In any case, the archive data is typically stored in a relatively inaccessible fashion. Thus, if one wants to retrieve the archived data, it is relatively difficult and time consuming. Additionally the format of the data will likely be very different from the originally stored material.

Even when the CU achieves an acceptable degree of retrieval speed, separate viewing platforms may be necessary to view, edit and otherwise use the data. Because each separate database may rely on a different viewing platform, a compatible, yet separate viewing platform may be necessary for data accessed from the multiple data bases. Utilizing separate viewing platforms for the test results is inconvenient, especially for those who do not have time to sufficiently study and learn the capabilities of the separate viewing platforms. What is desired is a simple and effective way of accessing large numbers of data records.

SUMMARY AND OBJECTS OF THE INVENTION

It is an object of this invention to provide an apparatus and method for generating, storing, and archiving analyzed data generated by an analyzer on various blood samples.

It is another object of the invention to provide an effective way of accessing the analyzed data in a fast and effective manner.

It is another object of this invention to provide an apparatus and method for effectively accessing both the most current data (the working data) and the older data (the archived data).

In accordance with the above objects and those that will be mentioned and will become apparent below, applicant has invented a computerized blood analyzer system, comprising:

- a clinical analyzer unit (CU) having a computer, the computer capable of issuing commands and instructions, including retrieval commands;
- a blood analyzer unit (AU) for analyzing blood samples electronically connected to a computer at the request and upon instructions from the CU and the AU generating test results;
- the computer having media for the storage of the test results, the media including an aggregate database for storing working data and archiving data, the aggregate database being symmetrical like so that the working and archived data is accessible by identical retrieval commands; whereby, the entire aggregate database is accessible by identical commands.

In an exemplary embodiment, the storage media is partitioned into at least two parts, including a working data storage part and an archive data storage part.

In another exemplary embodiment, the aggregate database includes a database for storing back-up data. The back-up database is symmetrical-like and is accessible by the same commands as the rest of the aggregate data base, including the working and archived data bases.

In another exemplary embodiment, the storage media includes a partition for the back-up database and the rest of the aggregate data bases.

In yet another exemplary embodiment, each part of the aggregate data is stored on separate storage media. For example, the working database is stored on the computer's main hard drive, the archived database is stored on the second hard drive and the back-up data bases is stored on a tape drive associated with the computer.

In another exemplary embodiment, the computer generates a data source selection for selecting a database. Actuation of the data source selection selects a database and directs the computer to access the selected database.

In another exemplary embodiment, the computer generates a search key. The computer displays the search key on the display. Actuation of the search key searches test results from the selected database.

In another exemplary embodiment, the computer generates a sort key. The computer displays the sort key on the display. Actuation of the sort key sorts test results from the selected database.

It is an advantage of the invention to provide an apparatus and a method used in connection with blood analyzing which includes an aggregate data appropriately partitioned.

BRIEF DESCRIPTION OF THE DRAWINGS

For a further understanding of the objects and advantages of the present invention, reference should be had to the following detailed description, taken in conjunction with the accompanying drawing, in which like parts are given like reference numerals and wherein.

DETAILED DESCRIPTION OF THE INVENTION

As used herein, aggregate data base may mean two or more data bases, which are entirely separate and independent. However, it may be preferable to have the aggregate data base comprise one data base with two or more tables and even more preferrable to have a single data base with symetrical data tables (SDTs). The invention contemplates the use of one or more data bases or tables in a single data base.

Figure 1:
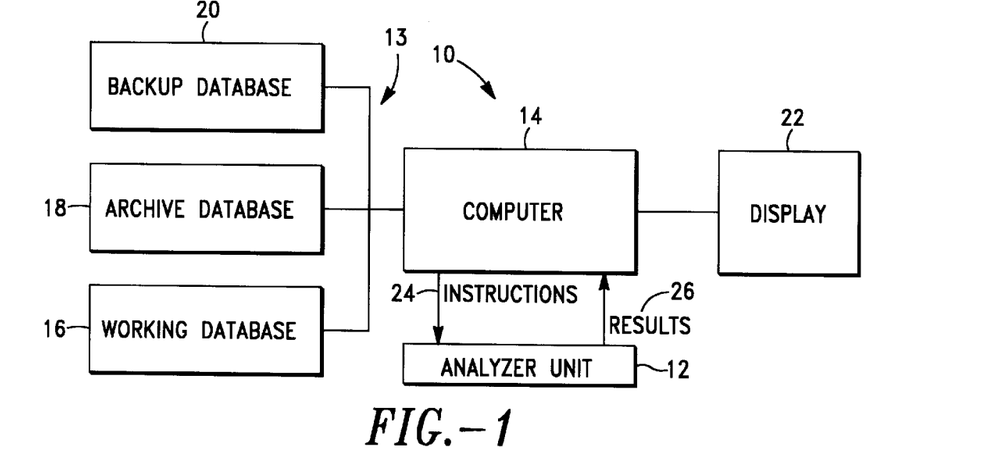
FIG. 1 shows a schematic diagram of an apparatus in accordance with the present invention.

With particular reference to FIG. 1, there is shown a schematic diagram of a computerized blood analyzer system for analyzing blood generally designated with the reference numeral 10. The system 10 includes a blood analyzer unit (AU) 12, a clinical analyzer unit (CU) having a computer 14, a storage media comprising an aggregate database 13 including a working database 16, an archive database 18, and a backup database 20. The computer 14 also includes a display 22.

The blood analyzer unit (AU) 12 analyzes blood samples. A blood sample is defined herein as including blood in various component form including samples of blood serum. Blood serum, in particular, is testable by the AU 12 for various composition materials including glucose. Although the AU is described as a blood serum tester, the AU may be replaced with a device which performs tests on any fluid including various biological fluids, industrial fluid mixtures, water and the like.

The computer 14 generates and transmits operational commands and instructions 24 including issuing retrieval commands. The blood analyzer unit 12 receives the operational instructions 24 from the computer 14. Pursuant to the instructions 24, the blood analyzer unit 12 performs a variety of specific blood analysis tests. From the blood analysis tests, the blood analyzer generates test results 26 and transmits the test results to the clinical analyzer unit computer 14. The computer 14 stores the test results 26 in the storage media as data. The data is characteristic of the test results. In the present embodiment, the AU includes a Model 912 Clinical Analyzer System as marketed by Hitachi Instruments, Inc. of San Jose, Calif.

The computer 14 is a general purpose computer having a processor, a memory system, and the display 22. The computer 14 electronically connects to the AU 12. The computer 14 is programmed to communicate instructions to the AU 12 and to receive test results from the AU 12.

The computer 14 includes a storage media comprising an aggregated database as described above and as shown in FIG. 1. The aggregate database 18 includes the working database 16. The back-up database 20 and archive database 18 maybe on the same or different storage media. For Example, the archive database or the back-up base or both could be on the internal and external hard disk drive. Each of the databases is symmetrical like meaning that the particular database format is quite similar and retrievable and storable by the same command orders and instructions for each portion of the aggregate database.

In the exemplary embodiment shown in FIG. 1. the databases are all configured on a single memory storage device, namely a hard disk drive. This enables rapid access of each of the databases. However, if large amounts of data are anticipated such as system would not be preferred. In such a case, the aggregate database comprises the working database 16 on the computer 14 hard disk drive. The archive database 18 on the computer 14 second hard disk drive and the back-up database 20 or in external tape drive associated with the computer 14. It will be appreciated that various combinations of storage media, both internal and external are within the scope of the invention and the above description is exemplary only.

The computer 14 communicates with the working database 16, the archive database 18 and the backup database 20. In another embodiment, the backup database 20 is configured on a removable memory storage device, namely a floppy disk drive. In another exemplary embodiment, the backup database 20 is configured on a removable storage device. Removeability of the media on which the backup database 20 is stored enables remote storage of data stored on the backup database 20. It will be appreciated that although the backup database 20 is configured on a memory storage device, the archive database can also be configured on removable memory storage device media such as a floppy disk, or a ZIP drive, or a swappable hard disk drive, for example.

The term "symmetrical-type" includes those data bases which are symmetrical, those data bases which have a substantial degree of structural symmetry, this includes similar data fields, organization and structure. A predetermined data format which enables access to the test results 26 by a computer having a single set of programmed access instructions would have an acceptable degree of symmetry to be a symmetrical-type database. An example of a predetermined format includes one in which stores data so that the test results are tabulated by result date, test type performed, patient name and sample number. Accordingly, in an embodiment of the present invention, the symmetrical-type data bases have data organized by result date, test type performed, patient name and sample number. Such organization enables the display of each symmetrical-type database by the computer 14.

The computer 14 is programmed with software to access symmetrical-type data bases. The data bases 16, 18 and 20 have a uniform data format. "Uniform data format" means a symmetrical-type data format which is readable by a single software engine.

The computer 14 selectively displays data from the data bases 16, 18 and 20 on the display 22. The symmetrical-type data bases 16, 18 and 20 enable the computer 14 to display selected test results from one database. Since data as used herein represents the test results 26, the terms "data" and "test results" may be used interchangeably.

Figure 2:
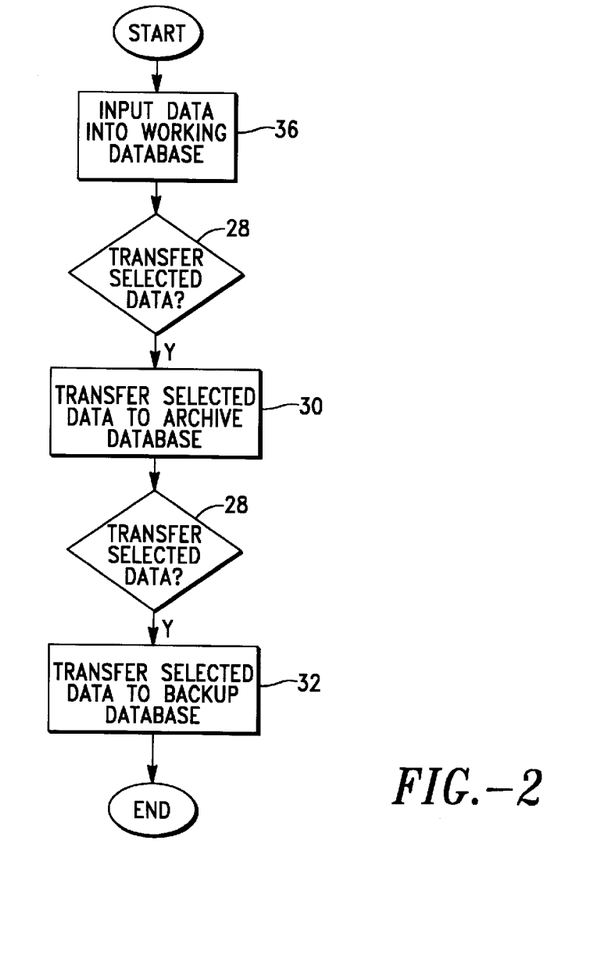
FIG. 2 shows a flow chart of a method of storing data in accordance with the present invention.

With particular reference to FIG. 2, there is shown a flow chart of a method of storing data in accordance with the present invention. The AU 12 generates test results and communicates data characteristic of the test results to the computer. When the computer 14 receives test results from the AU 12, the computer 14 automatically inputs the data into the working database 16. The step of inputting data into the working database is designated with the reference numeral 36. The operator has the option of selectively transferring data 28 and selectively storing the transferred data in the archive database 30, the backup database 32, or both.

In an alternate embodiment, the computer is programmed to periodically transfer data from the working database 16 into the archive database 18. This periodic transfer of data frees the working database from cumulative data which may distract the user. An operator may access the working database to find only the test results from the same day. This enables an operator to disregard cumulative data which is archived.

The length of time for periodically transferring of data is programmable. In one embodiment, the time from one hour to seven days, and preferably, between two and four days.

Figure 3:
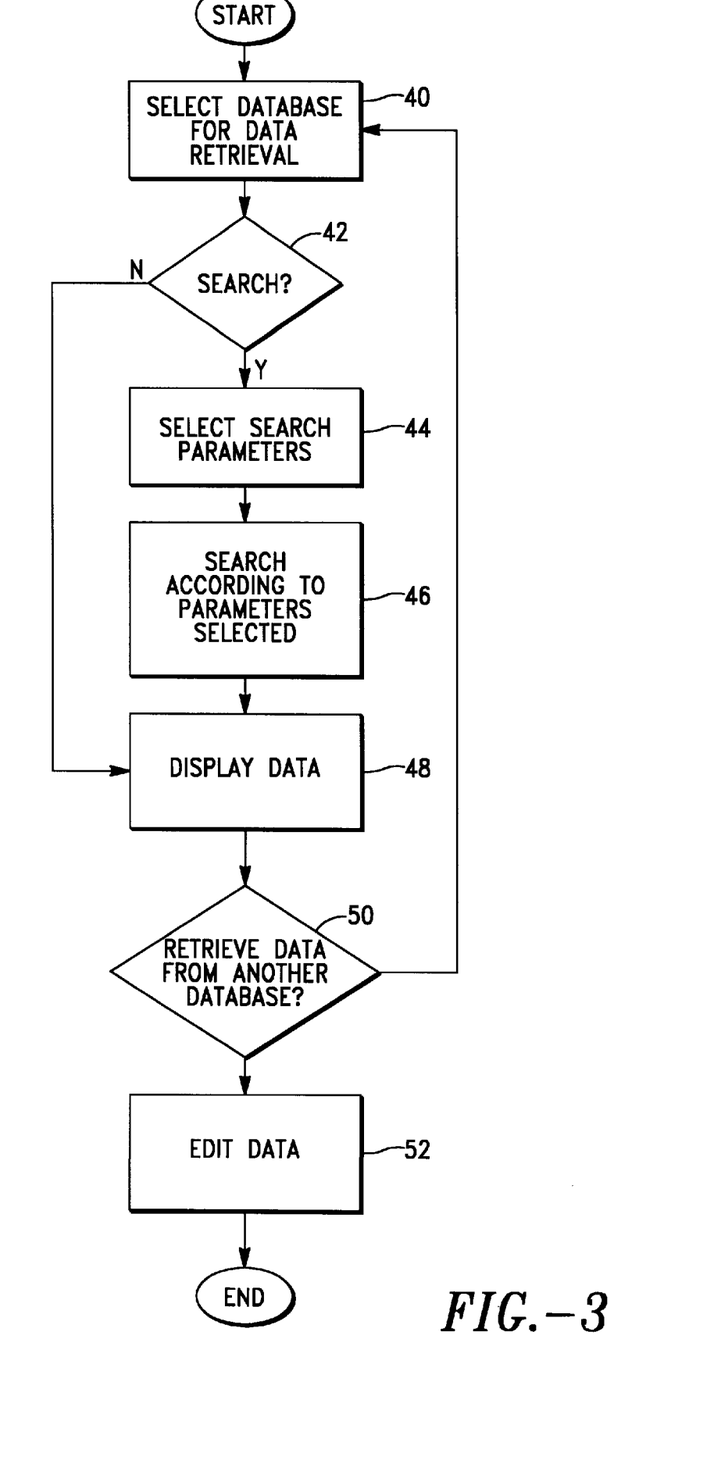
FIG. 3 shows a flow chart of a method of searching data in accordance with the present invention.

With particular reference to FIG. 3, there is shown a flow chart of a method of searching for particular test results in accordance with the present invention. First a database is selected for data retrieval. The step of selecting a database is designated by the reference numeral 40. The display 22 (FIG. 1) normally displays data 48 from the selected database. The operator has an option of viewing the displayed data, or initiating a search 42 to filter the amount of data displayed. When a search 42 is initiated, the operator searches the selected database. Search parameters 44 generated by an operator are manually inputted into the computer 14. The computer 14 performs the search 46. The search 46 queries the selected database(s) within the aggregate database and generates the appropriate search results. The computer displays 48 the search results on the monitor.

It will be appreciated that upon viewing the search results on the display, the operator has the option to perform additional searches from any selected database. Upon completion of the additional search, the display simultaneously displays search results from the additional search with the results from any prior searches.

In another embodiment, the search results are displayed consecutively, where data from one database is displayed, and then replaced by data from another database. When the search results are displayed, the operator is able to edit the search results.

Figure 4:
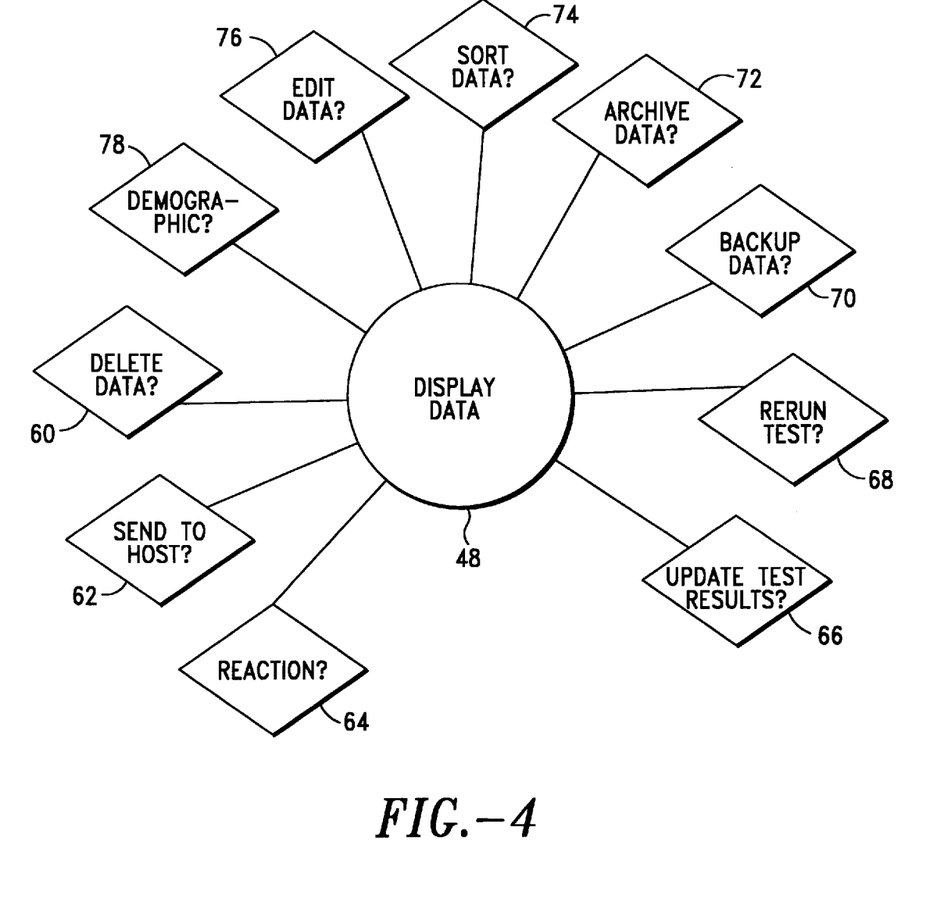
FIG. 4 shows a data flow chart diagram for a clinical analyzer system in accordance with the present invention.
Figure 5:
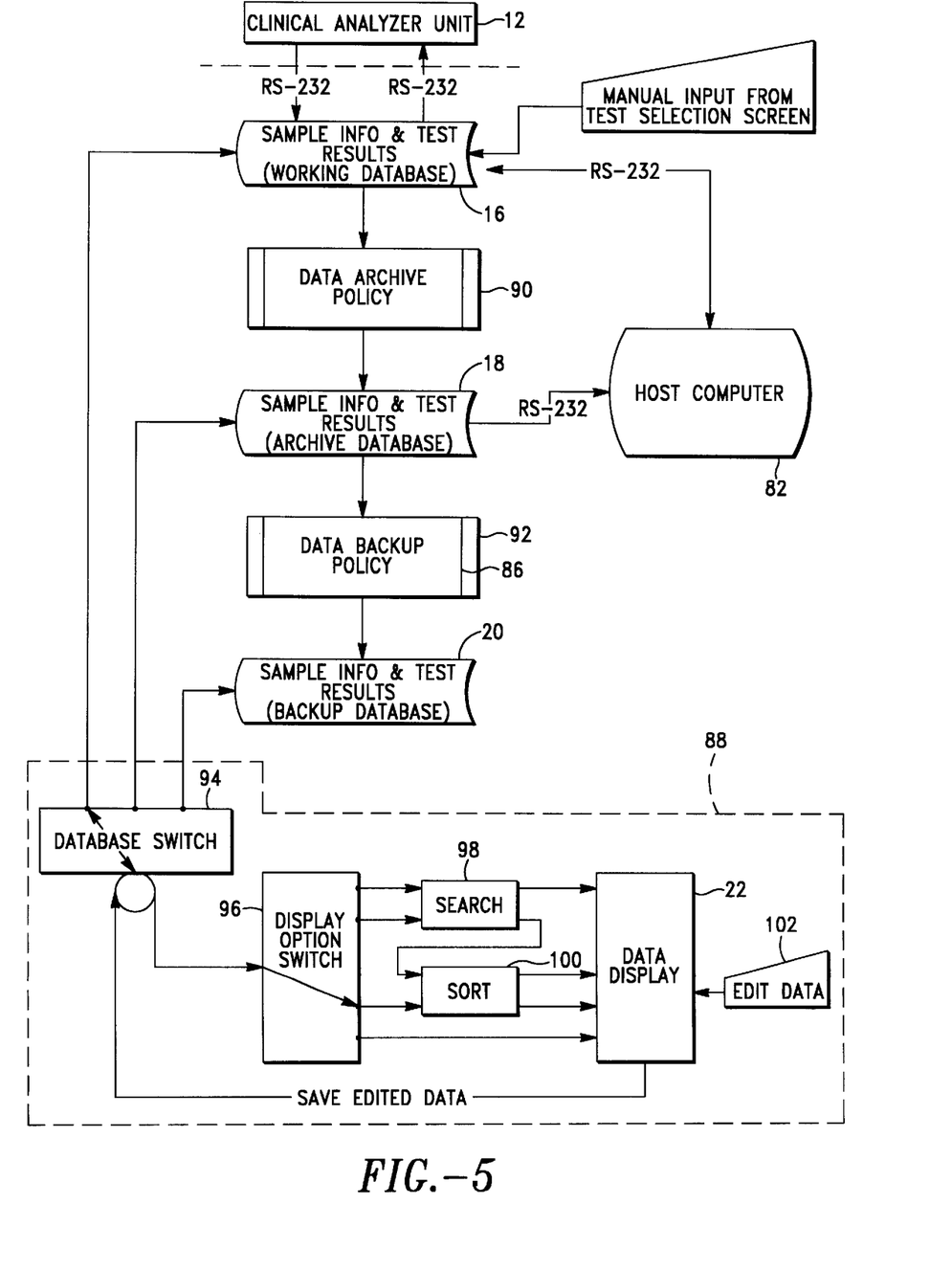
FIG. 5 shows a data review screen in accordance with the present invention.

With particular reference to FIG. 4, there is shown a data flowchart diagram in accordance with the present invention. The data flow chart diagram includes the clinical analyzer unit AU 12; a host computer system 84; a software engine 86 and a display system 88. The display system 88 includes a database switch 94; a display option switch 96; a search module 98; a sort module 100; the display 22 and an editor 102.

The database switch 94 communicates with the software engine 86 for selecting a particular database from the aggregate database. In one exemplary embodiment shown in FIG. 4, the database switch 94 actuates a selected database in response to operator input. This input is communicated in a variety of ways including utilizing the display interface in conjunction with an input device such as a mouse.

The software engine 86, the display system 88 and the database switch 94 are implemented by the computer 14 (FIG. 1). The software engine 86 links the computer 14 in communication with the working database 16, the archive database 18 and the backup database 20. The software engine 86 includes a data archive policy 90 and a data backup policy 92. The data archive policy 90 and the data backup policy 92 are pre-programmed in one embodiment of the invention to enable periodic backup and periodic archiving of test results. In another exemplary embodiment, the data archive policy 90 and data backup policy 92 are manually programmed via the data display interface in conjunction with an input device such as a mouse.

An example of a suitable data archive policy is to normally store data in the working database 16 and to move the stored data from the working database 16 to the archive database 18 every three days. The archive database 18 provides a cumulative record of data which was generated by the AU. It is the newly generated data, however, which is most likely needed by an operator. Accordingly, the benefit of archiving data is so that data in the working database 16 will be accessible when needed. Older archived data (cumulative data) is less likely to be needed by an operator so the cumulative data is stored separately. The archived data is accessed by a search as desired and may be displayed in sorted form.

In one embodiment of the data backup policy 92, operates simultaneously with movement of the data between the working database 16 and the archive database 18. In a variation of this embodiment, the data backup policy 92 mirrors the data which is being moved and stores the mirrored data in a separate location, such as on a separate disk drive. The data backup policy 92 may be programmed to also mirror the entire archive database 18. Accordingly, the data backup policy 92 provides redundancy in case a memory storage device fails, or in case the archive and working data bases, 18 and 16 respectively are corrupted.

The software engine 86 communicates electronically with the AU 12 and the host computer system 84 via standard RS-232 cables. In other embodiments, however, the RS-232 cables may be replaced, for example, by a wireless interconnection. In particular, the host computer system 84 may have a digital satellite link between itself and the software engine 86. Accordingly, the software engine 86 is accessible by a remote user having a host computer system 84. The remote user may perform blood tests with the clinical analyzer unit 12 via the host computer system 84 and to access the data bases 16, 18 and 20.

The operator inputs a search query to the software engine 86. The software engine 86 filters data from selected data bases. Particularly, the software engine 86 simultaneously searches the selected data bases in response to the search query to generate search results. The software engine 86 compiles the results of the search query and displays the results on the display 22.

The data bases 16, 18 and 20 are symmetrical, meaning they have similar data fields, in organization and structure to enable the computer to access data from all the data bases with the same commands and instructions. The software engine 86 instructs the computer to utilize the uniform data format and to implement the data archive policy.

In one exemplary embodiment, the backup database 20 cumulatively mirrors the working database 16 while the archive database 18 periodically stores data from the working database 16.

The database switch 94 interconnects the display system 88 with the software engine 86 to enable the display of data from each database. The display system 88 has a display option switch 96 for selectively communicating search results to the display. The display option switch 96 directs the data flow through the search module 98 or through the sort module 98, or both depending upon the instructions provided by the operator.

The host system 84 generates AU 12 instructions and communicates the instructions to the software engine 86. The software engine 86, in turn, communicates the instructions to the AU 12 (FIG. 1). The AU 12 analyzes blood and generates data characteristic of blood analysis test results.

The host system 84 communicates with the software engine 86 for accessing each database 16, 18 and 20 and displaying test results. The software engine 86 receives test results from the AU 12, compiles the test results and store the test results. The stored test results are thus accessible by the host computer system 84.

Figure 6:
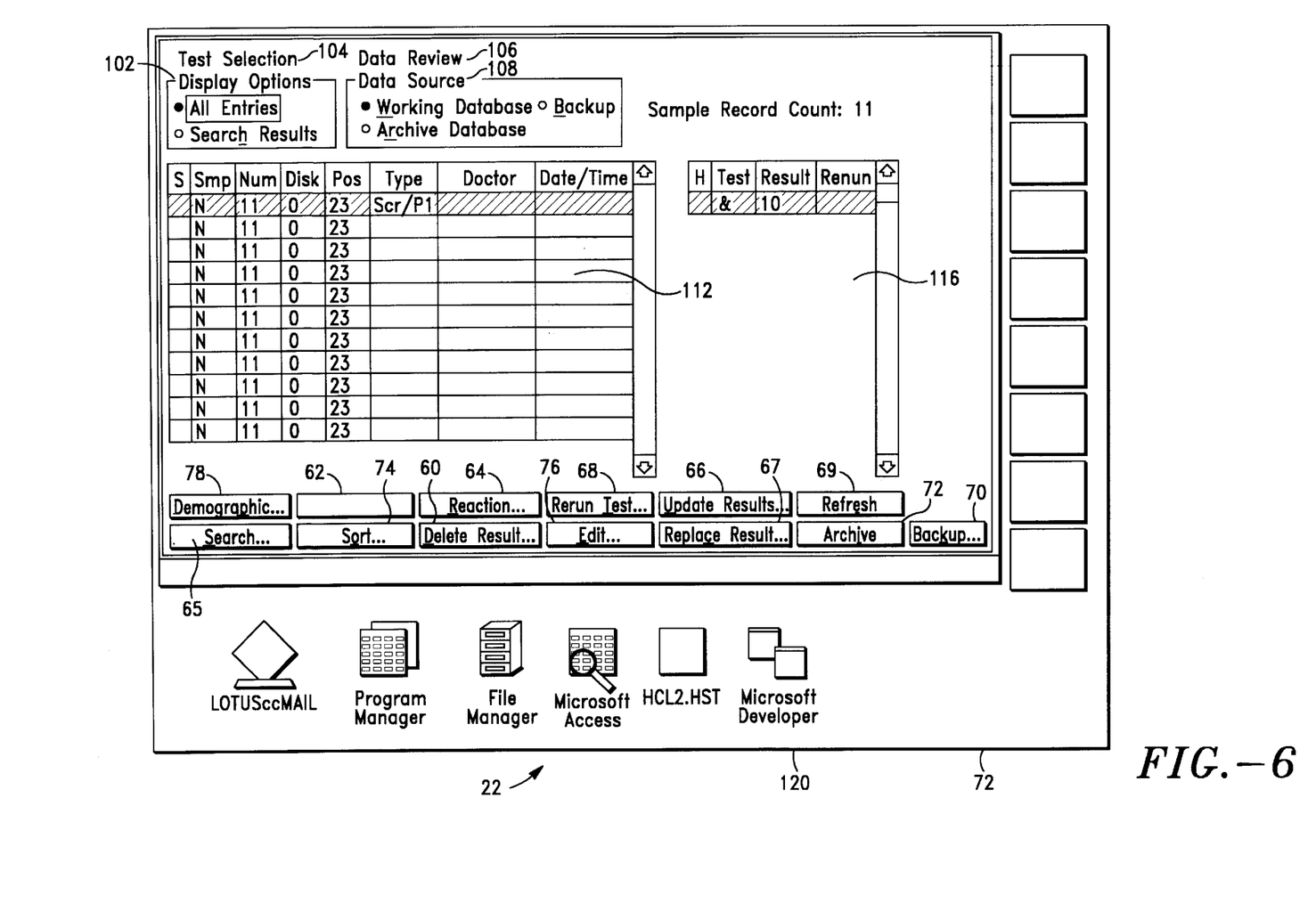
FIG. 6 shows an examplary embodiment of the display of the present invention.

With particular reference to FIG. 6 there is shown an exemplary embodiment of the display of the present invention. The software engine generates a Windows™ compatible front end 120 and presents the front end 120 on the display 22. The display, in cooperation with the software engine 86, alternatingly displays a test selection screen 104 and a data review screen 106 In FIG. 6, the data review screen is shown.

The test selection screen 104 provides an interface for selecting and initiating a desired test for the AU 12 to perform.

The data review screen 106 includes a first window 110 having a table 112. The data review screen 106 displays the test results on the table 112. The data review screen 106 includes a second window 116 which tabulates test information.

The data review screen 106 includes a data source selection 108 and a display options selection 102 for selecting a desired database and display options, respectively. Actuation of the data source selection 108 selects a database and directs the computer to access the selected database. Actuation of each selection key and selection may be accomplished with a mouse, keyboard or other input device. The data source selection includes a working data base, an archive data base, and a backup database.

The display options selection 102 normally enables a user to fully display the selected database. Actuation of a portion of the display options selection 102 enables a user to display only the search results.

The computer 14 generates multiple keys representing various functions which the software engine will perform in response to actuation of the keys. The keys including a delete result key 60; a demographic key 78, a send to host key 62, a reaction key 64, a re-run test key 68, an update search results key 66, a refresh key 69, a search key 65, a sort key 74, an edit key 76, a replace results key 67, an archive key 72 and a backup key 70. When the computer displays data, an operator may chose to: delete data; send data to a host; react; update test results; rerun a test; backup data; archive data; sort data; edit data and request a demographic by actuation of the appropriate key.

Actuation of the search key 65 searches test results from the selected database. Actuation of the sort key 74 sorts test results from the selected database. Actuation of the archive key 72 saves the selected test results in the archive database. Actuation of the backup key 70 saves the selected test results in the archive database. Actuation of the edit key 76 enables user input to edit the displayed test results. Actuation of the delete result key 60 enables deletion of the displayed test results from the computer. Actuation of the refresh key 69 updates test results from the selected database. Actuation of the re-run test key 68 causes the computer to send an instruction set to the AU to cause the AU to repeat a selected test. Actuation of the send-to-host key 62 causes the computer (FIG. 1) to send selected test results to the host computer system 84 (FIG. 4). Actuation of each aforementioned keys is accomplished by using a point and click mouse which attaches to the computer.

Data is selected from the display 22 by, for example, highlighting the data with a cursor or mouse. Selected data is stored in the archive database by actuating the archive key 72. Selected data is stored in the backup database by actuation of the backup key 70.

An operator actuates the test selection screen 104 to specify one or more tests which the AU 12 (FIG. 1) is to perform. The software engine 86 (FIG. 4) communicates the test selection to the AU 22 and causes the AU 22 to perform the specified test(s). In one embodiment, instructions for analyzing blood are generated on the test selection screen 104 by an operator. In another embodiment, the blood test selection is preprogrammed.

Pursuant to the instructions, the AU 22 performs at lease one desired test and generates test results characteristic of the blood analysis tests which were performed.

The test results are displayed from the working database on the display. The display offers a symmetrical-type database selection of data bases where selected test results may be re-stored. Selecting a database from the display stores the selected test results in the selected database.

An operator has an option to recall test results. These test results are displayed. The operator may edit the selected test results, select a new database from the display, and move the selected test results to another database.

Various modifications and changes in the invention as described may be made in accordance with the scope of the present invention. For example, the configuration of each database or table and of the front end may change. Additionally, the present invention is useful with blood analyzers of various sorts. The present invention is limited in scope only by the appended claims.

What is claimed:

1. A computerized blood analyzer system, comprising:
   a clinical analyzer unit (CU) having a computer, the computer capable of issuing commands and instructions, including retrieval commands;
   a blood analyzer unit AU electronically connected to the CU for analyzing blood samples at the request and upon instructions from the CU and generating test results
   the computer having media for storing of the test results, the media including an aggregate database for storing working data and archived data, the aggregate database being symmetrical-like so that the working and archived data are accessible by the same retrieval commands, the storage media being partitioned into at least two parts, including a working data storage part and an archive data storage part, whereby, the entire aggregate database is accessible by the same commands from the CU.

2. A computerized blood analyzer system, comprising:

a clinical analyzer unit (CU) having a computer, the computer capable of issuing commands and instructions, including retrieval commands;

a blood analyzer unit AU electronically connected to the CU for analyzing blood samples at the request and upon instructions from the CU and generating test results the computer having media for storing of the test results, the media including an aggregate database for storing working data and archived data, the aggregate database being symmetrical-like so that the working and archived data are accessible by the same retrieval commands, the aggregate database including a back-up database for storing back-up data, the back-up database being symmetrical-like and being accessible by the identical retrieval commands as the other parts of the aggregate database, whereby, the entire aggregate database is accessible by the same commands from the CU.

3. A computerized blood analyzer system as set forth in claim 2, wherein the storage media includes a partition for the back-up data.

4. A computerized blood analyzer system as set forth in claim 2, wherein each part of the aggregate data is storable on separate or the same media.

5. A computerized blood analyzer system, comprising:

a clinical analyzer unit (CU) having a computer, the computer capable of issuing commands and instructions, including retrieval commands;

a blood analyzer unit AU electronically connected to the CU for analyzing blood samples at the request and upon instructions from the CU and generating test results the computer having media for storing of the test results, the media including an aggregate database for storing working data and archived data, the aggregate database being symmetrical-like so that the working and archived data are accessible by the same retrieval commands, wherein the computer generates a data review selection screen and the computer displays the data review selection screen on the display for reviewing and/or edit test results, whereby, the entire aggregate database is accessible by the same commands from the CU.

6. A computerized blood analyzer system, comprising:

a clinical analyzer unit (CU) having a computer, the computer capable of issuing commands and instructions, including retrieval commands;

a blood analyzer unit AU electronically connected to the CU for analyzing blood samples at the request and upon instructions from the CU and generating test results the computer having media for storing of the test results, the media including an aggregate database for storing working data and archived data, the aggregate database being symmetrical-like so that the working and archived data are accessible by the same retrieval commands, wherein the computer generates a test selection screen, the computer displays the test selection screen on the display, and the test selection screen provides an interface for selecting and initiating a desired test for the AU to perform, whereby, the entire aggregate database is accessible by the same commands from the CU.

7. A computerized blood analyzer system, comprising:

a clinical analyzer unit (CU) having a computer, the computer capable of issuing commands and instructions, including retrieval commands;

a blood analyzer unit AU electronically connected to the CU for analyzing blood samples at the request and upon instructions from the CU and generating test results the computer having media for storing of the test results, the media including an aggregate database for storing working data and archived data, the aggregate database being symmetrical-like so that the working and archived data are accessible by the same retrieval commands, wherein the computer generates a data source selection for selecting a database, actuation of the data source selection selects a database and directs the computer to access the selected database, whereby, the entire aggregate database is accessible by the same commands from the CU.

8. A computerized blood analyzer system as set forth in claim 7, wherein the computer generates a search key, the computer displays the search key on the display, actuation of the search key searches test results from the selected database.

9. A computerized blood analyzer system as set forth in claim 7, wherein the computer generates a sort key, the computer displays the sort key on the display, actuation of the sort key sorts test results from the selected database.

10. A computerized blood analyzer system as set forth in claim 7, wherein the computer displays test results and an archive key, the computer includes an archive database, actuation of the archive key saves the selected test results in the archive database.

11. A computerized blood analyzer system as set forth in 7, wherein the computer displays test results and a backup key, the computer includes a backup database, actuation of the backup key saves the selected test results in the archive database.

12. A computerized blood analyzer system as set forth in 7, wherein the computer displays test results and an edit key, actuation of the edit key enables user input to edit the selected test results.

13. A computerized blood analyzer system as set forth in claim 7, wherein the computer displays test results and a delete key, actuation of the delete key enables deletion of the displayed test results from the computer.

14. A computerized blood analyzer system as set forth in claim 7, wherein the computer displays test results and a refresh key, actuation of the refresh key updates test results from the selected database.

15. A computerized blood analyzer system as set forth in claim 7, wherein the computer displays test results and a re-run test key, actuation of the re-run test key causes the computer to send an instruction set to the AU to cause the AU to repeat a selected test.

16. A computerized blood analyzer system as set forth in claim 7, wherein the computer displays test results and a send-to-host key, actuation of the send-to-host test key causes the computer to send selected test results to a host system.

17. A computerized blood analyzer system as set forth in claim 7, wherein the computer has a search engine for performing data searches; the computer displays a display options selection, the computer normally displays test results from all entries, the display options selection selectively displays search results when a search has been performed.

18. A computerized blood analyzer system as set forth in claim 7, wherein the data source selection includes a working database, an archive database, and a backup database.

* * * * *